United States Patent
Wagner et al.

(10) Patent No.: US 6,798,517 B2
(45) Date of Patent: Sep. 28, 2004

(54) HANDHELD, PORTABLE COLOR MEASURING DEVICE WITH DISPLAY

(75) Inventors: Gregg Wagner, Boulder, CO (US); Gary Emerson, Golden, CO (US)

(73) Assignee: Color-Spec Technologies, Inc., Denver, CO (US)

( * ) Notice: Subject to any disclaimer, the term of this patent is extended or adjusted under 35 U.S.C. 154(b) by 0 days.

(21) Appl. No.: 09/854,344

(22) Filed: May 11, 2001

(65) Prior Publication Data

US 2002/0036778 A1 Mar. 28, 2002

Related U.S. Application Data

(60) Provisional application No. 60/236,304, filed on Sep. 28, 2000.

(51) Int. Cl.[7] .................................................. G01J 3/50
(52) U.S. Cl. ........................................ 356/406; 356/407
(58) Field of Search ................................ 356/402, 405, 356/406, 407

(56) References Cited

U.S. PATENT DOCUMENTS 5,926,262 A  *  7/1999  Jung et al. .................... 356/416
6,157,454 A  * 12/2000  Wagner et al. ............... 356/407

FOREIGN PATENT DOCUMENTS

WO    WO 96/13709    *  5/1996  ................. 356/419

* cited by examiner

Primary Examiner—F. L. Evans
(74) Attorney, Agent, or Firm—Edwin H. Crabtree; Ramon L. Pizawo; Donald W. Margolis

(57) ABSTRACT

A handheld, portable color measuring device for measuring the primary colors of red, green and blue in a color target to be analyzed and connected to a built-in LCD display or connected to a separate personal computer. The color measuring device includes an elongated color measuring probe housing. A hollow cone shaped probe tip is attached to one end of the probe housing. A target contact end of the probe tip is placed against a color target to be measured. Inside the probe housing is a battery powered white LED light source connected to a color measurement switch. When the measurement switch is actuated, the white light source illuminates the color target surrounded by the target contact end of the probe tip. A light pipe is centered inside the probe housing and inside a portion of the probe tip. The light pipe captures the reflected light off the color target and projects the captured light onto a 3 color (RGB) sensor. The sensor collects an analog light signal which is made up of percentages of red, green and blue. The light signal is amplified and converter to a digital signal using an A/D converter. The A/D converter is part of a microprocessor mounted on a printed circuit board inside the probe housing. The digital signal is processed by the microprocessor and the percentages of red, green and blue are displayed on the LDC display or on the screen of the computer.

16 Claims, 4 Drawing Sheets

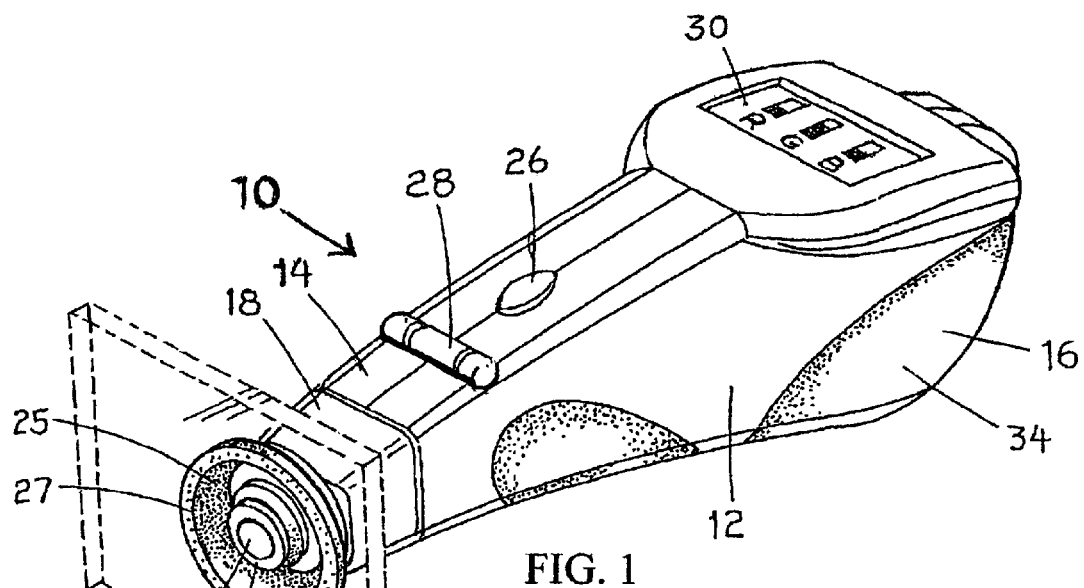
FIG. 1
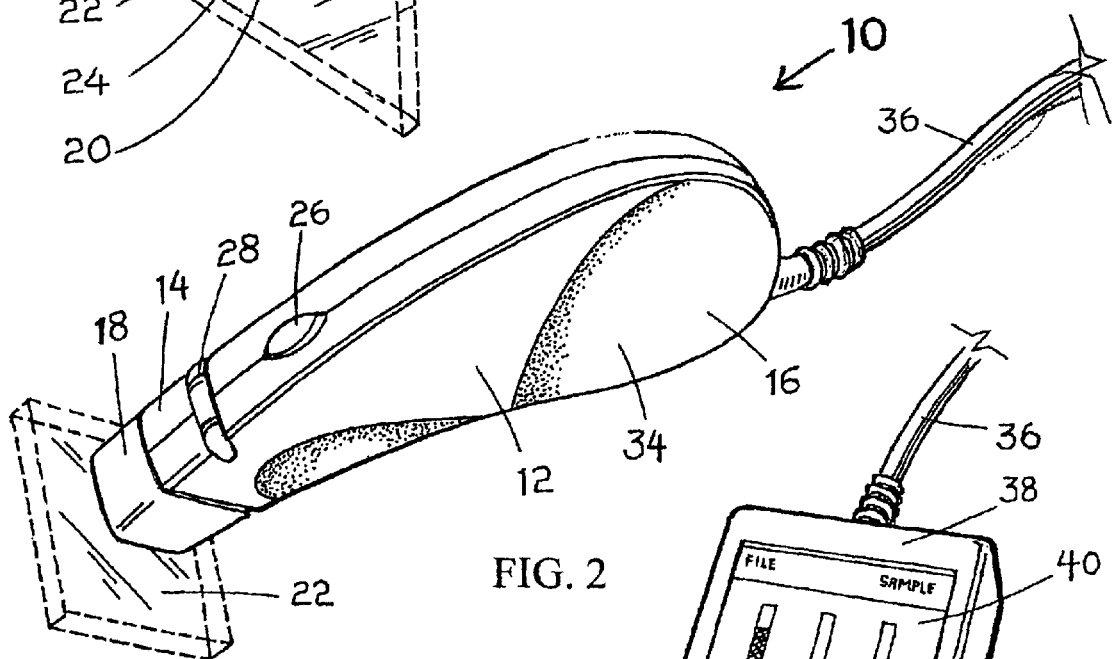
FIG. 2
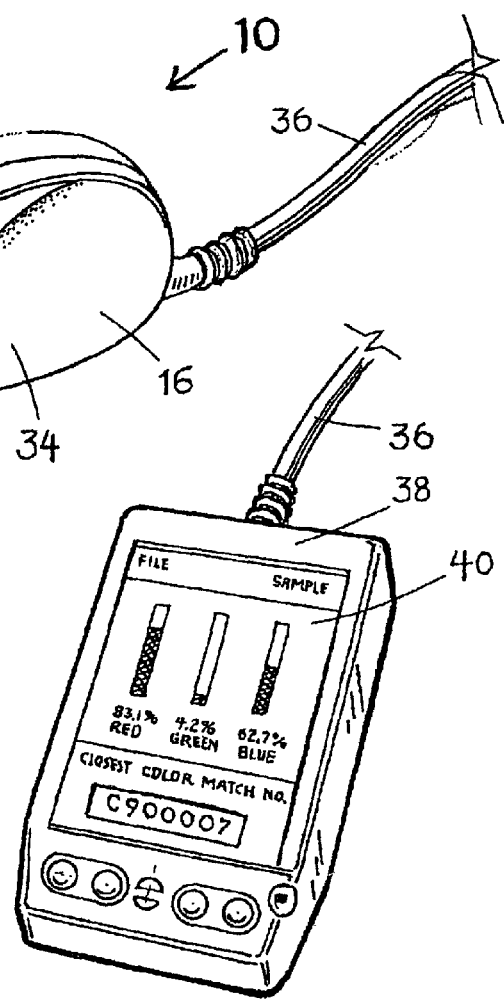

HANDHELD, PORTABLE COLOR MEASURING DEVICE WITH DISPLAY

This application is based on a provisional patent application filed in the U.S. Patent and Trademark Office on Sep. 28, 2000, having Ser. No. 60/236,304 and a title of "COLOR COMPARISON DEVICE FOR USE WITH POCKET PC OR PALMTO COMPUTERS"

BACKGROUND OF THE INVENTION (a) Field of the Invention

This invention relates to a device used for measuring and analyzing colors and more particularly, but not by way of limitation, to a handheld, portable color measuring device adapted for use with and without a personal computer and used for measuring colors of various objects.

(b) Discussion of Prior Art

Heretofore in many color measuring applications, there is a continuous need to analytically measure a color of an object, to compare colors of different materials or compare objects with each other and to reference a color standard. For example, matching an injection molded product to a customer's color reference standard or matching paint to a paint manufacturer's paint swatch.

There are many industries where there are benefits to having an analytical means to measure color. For example, on today's market there are color measurement devices which can analytically measure color, but they are generally very expensive. Also, these devices are complex in operation which limits the number of users. With the advent of new computer technologies related to portable personal computers, an accurate color measuring device, as disclosed herein, is now affordable and easily made portable.

U.S. Pat. No. 5,838,451 to McCarthy discloses a system for optoelectronic spectral analysis. The system uses an apparatus having multiple LEDs disposed around a photosensor. The photosensor and LEDs are mounted on a common substrate along with a lens for coupling light to and from a color target.

U.S. Pat. No. 5,844,680 to Sperling describes a device and process for measuring and analyzing spectral radiation. The device includes a wavelength spectra having multiple sources and sensors which overlap to provide a full spectrum color measurement within a color range of interest.

U.S. Pat. No. 5,691,701 to Wohlstein et al, discloses a fluid or vapor diagnostic device. The device uses multicolored LED's for sensing a color of a gas or fluid. Also, the device uses fiber optics for coupling light from the gas, fluid or vapor.

U.S. Pat. Nos. 5,851,113 to Jung, et al. and 5,690,486 to Zigelbaum disclose two different types of apparatus and method for measuring the color of teeth. The two dental devices are used to determine the correct color of restorative dental material to use when repairing a damaged tooth.

U.S. Pat. No. 6,157,454 to Wagner et al. discloses a miniature colorimeter for taking color measurements of an object. The object is illuminated using a light pipe with a light source made up of red, green and blue LED's. A light sensor senses the reflected light from the object. The light sensor is connected to a microprocessor and a display panel.

While the above systems and devices are used for various types of color spectral analysis, none of them specifically disclose the unique structural features, functions, objects and advantages of the subject handheld color measuring device.

SUMMARY OF THE INVENTION

In view of the foregoing, it is a primary objective of the subject invention to provide a unique color measuring device which is lightweight, handheld, inexpensive and portable.

Another object of the color measuring device can be a free standing unit including its own built in display. Also, the device can be connected to a personal computer such as a Compact Companion, a Palm Pocket PC, a Handspring Pocket PC and the like for storage data and providing a visual display.

Yet another object of the color measuring device is by using a LED white light source and a single 3 color sensor, percentages of red, green and blue and other multiple colors can be detected either simultaneously or sequentially. Also, the sensor includes color coating for more controllable and consistent wavelength output, thereby eliminating a need for notch filters.

A further object of the invention is the 3-color sensor is connected to an analog printed circuit board, which reduces transient noise levels by eliminating the use of cables from the sensor to the circuit board. This feature provides for a better signal to noise ratio thus enabling improved discrimination of colors in dark regions.

The color measuring device includes an elongated color measuring probe housing having a first end portion and a second end portion. A hollow cone shaped probe tip is attached to the first end portion of the probe housing. A target contact end of the probe tip is placed against a color target to be measured. Inside the first end portion of the probe housing is a battery powered white LED light source connected to a color measurement switch. When the measurement switch is actuated, the white light source illuminates the color target surrounded by the target contact end of the probe tip.

A light pipe is centered inside the first end portion of the probe housing and inside a portion of the probe tip. The light pipe captures the reflected light off the color target and projects the captured light onto a 3 color (RGB) sensor. The 3-color sensor collects a light signal, which is made up of percentages of red, green and blue. The percentages may be detected simultaneously or sequentially. An analog light signal is amplified and converter to a digital signal using an A/D converter. The A/D converter is part of a microprocessor mounted on a printed circuit board in the probe housing. The digital signal is transmitted from the microprocessor to a liquid crystal display, LCD, mounted in the second end of the probe housing. Also, the digital signal can be transmitted via a communications cable, such as a RS232 serial I/O port cable, an USB interface cable, or via an expansion slot of a pocket PC. The computer is used for storing data and displaying the color measurement on a display screen and comparing the measurement with similar color matches. Also, the computer allows for interfacing to the Internet, which provides downloading additional color lookup tables or transfer of color sample data.

These, and other objects of the present invention, will become apparent to those familiar with different types of color analyzers and devices used in measuring color when reviewing the following detailed description, showing novel construction, combination, and elements as herein described, and more particularly defined by the claims. It being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which:

FIG. 1 is a perspective view of the subject handheld, portable color measuring device having a hollow cone shaped probe tip in a first end of an elongated probe housing. The color measuring device also includes a built in display in a second end of the probe housing.

FIG. 2 is a perspective view of another embodiment of the handheld, portable color measuring device with the hollow cone shaped probe tip in the first end of the probe housing, and the second end attached to a communications cable. The communications cable is dependent on the type of computer device. The cable may be a standard RS232 serial I/O port cable, an USB interface cable, or via the expansion slot of a pocket PC.

DESCRIPTION OF THE PREFERRED EMBODIMENTS

Figure 3:
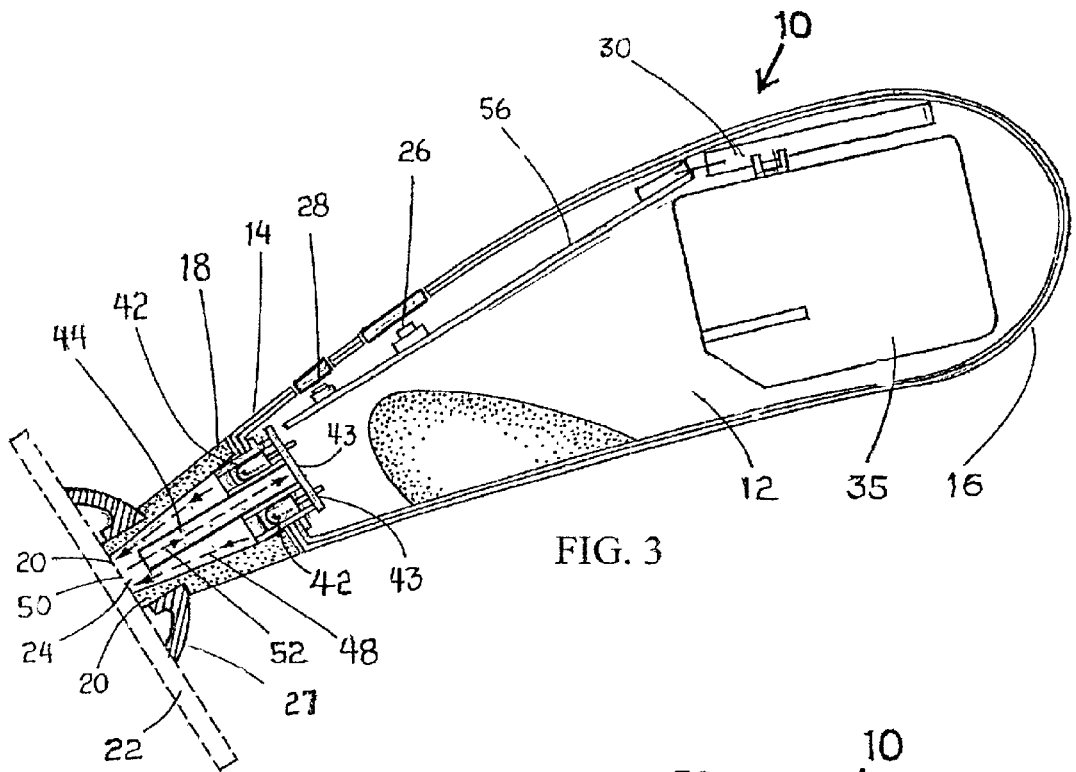
FIG. 3 is a side sectional view of the handheld portable color measuring device shown in FIG. 1 and illustrating the internal components inside the elongated probe housing.

In FIG. 1, a perspective view of the handheld, portable color measuring device is shown having general reference numeral 10. The color measuring device 10 includes an elongated color measuring probe housing 12 having a first end portion 14 and a second end portion 16. A hollow probe tip 18 is attached to the first end portion 14 of the probe housing 12. A target contact end 20 of the probe tip 18 is shown placed against a color target 22 for measuring and analyzing the target's color. The contact end 20 includes an annular contact end opening 24 for receiving light there through. A cap with a white coating, not shown in the drawings, is used for receiving around the contact end 20 for calibrating the device 10 to a white standard prior to taking color measurements.

The probe tip 18 can also include a light shield 25 having a flexible annular ring 27. The light shield 25 is used when there is a rough surface on the color target 22. Obviously, the light shield 25 may or may not be used if the target has a smooth surface. The light shield 25 engages a portion of the target 22 and prevents ambient light from entering into the target area and assuring an accurate color measurement reading. The reading is taken when white light is shown "on" and "off" the target when analyzing its color. In the drawings, the color target 22 is shown in dashed lines. The color target 22, as mentioned above, may be various colored objects and items such as an injection molded products, paint samples from a home, building or vehicle, paint swatches and the like.

Figure 4:
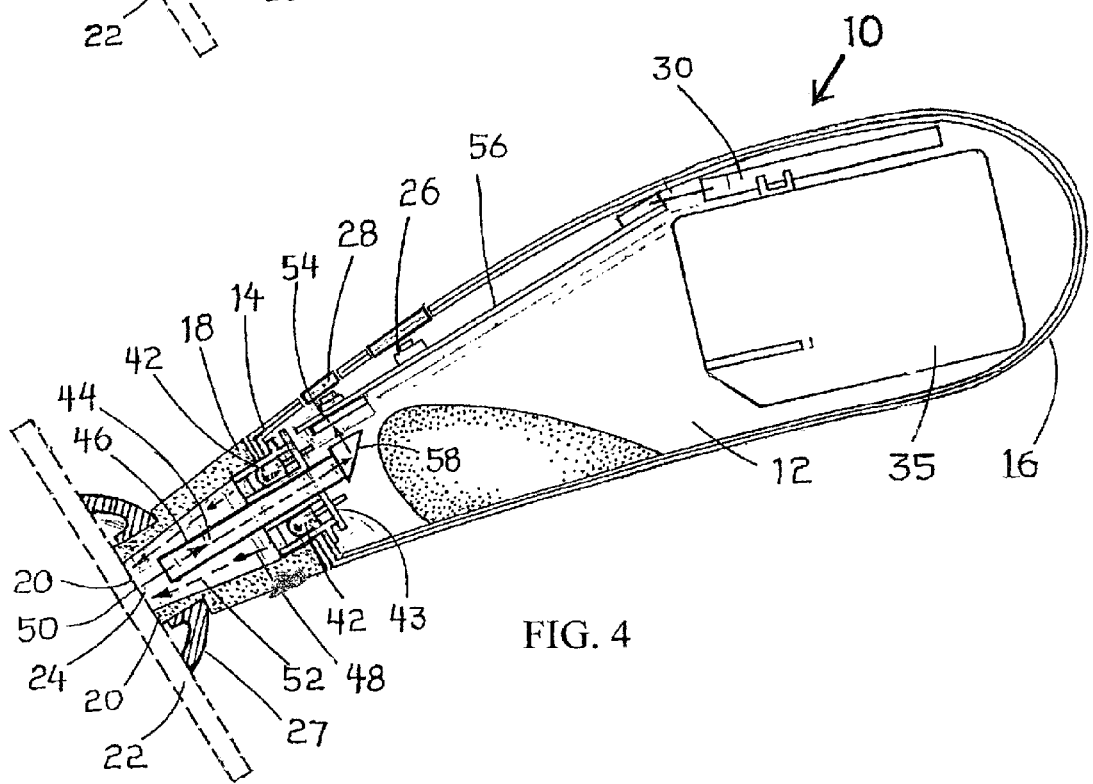
FIG. 4 is another side sectional view of the handheld portable color measuring device shown in FIG. 1 and illustrating the internal components inside the housing with a light pipe having a turning prism for reflecting white light received from a target onto a 3 color sensor or photodiode.
Figure 5:
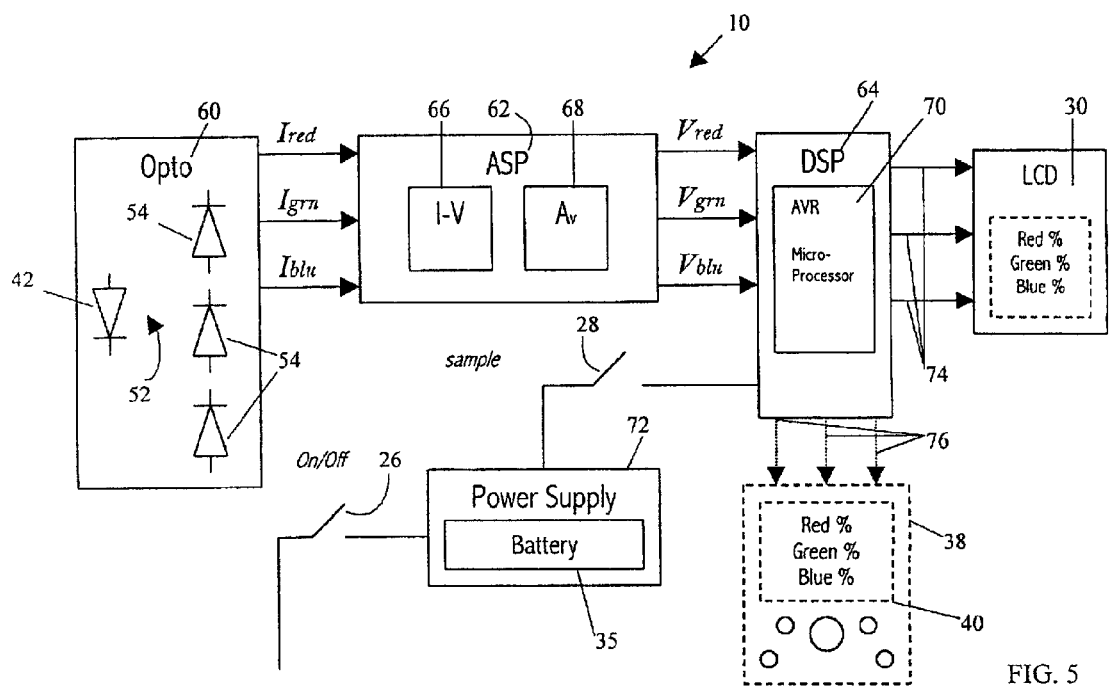
FIG. 5 is a circuit diagram of the optical and electrical components making up the color measuring device.

The exterior of the device 10 includes an on/off switch 26 for turning the unit "on" and "off" and a color measurement switch 28 for illuminating the target 22 and receiving back a reflected analog color signal. The probe housing 12 also includes in the top of the second end portion 16 a built-in liquid crystal display 30 or LED. The display 30 will typically show color percentages of red, green and blue in the color target 22 along with a number of the closest color match stored in memory. The display 30 can also display machine status, calibration of the device 10 and the state of the power source. Further, the probe housing 12 has a first side 32 with a sliding door 34 for opening into the interior of the housing and changing out a 6 volt battery 35. The battery 35 is shown in FIGS. 3–5.

In FIG. 2, a perspective view of another embodiment of the handheld, portable color measuring device 10 is illustrated. In this drawing, the probe housing 12 is shown without the built-in liquid crystal display 30 and without the light shield 25. The second end 16 of the probe housing is shown attached to a communications cable 36 for connecting the color measuring device 10 to a pocket personal computer 38 and having a visual display 40. The personal computer 38, for example, can be a Compact Companion, a Palm Pocket PC, a Handspring Pocket PC and the like for storing color information data and providing a color analysis on the visual display 40.

The visual display 40 illustrates, for example, a color analysis of 63.1% Red, 4.2% Green and 62.7% Blue. Based on stored data in the device's memory in a microprocessor in the device 10 or in memory in the computer 38, the closest color match number is C900007.

In FIG. 3, a side, sectional view of the handheld portable color measuring device 10 as shown in FIG. 1 is illustrated. In this drawing the internal components inside the elongated probe housing 12 are shown.

Inside the first end portion 14 of the probe housing 12 is a white LED light source 42 connected to the color measurement switch 28 and mounted on an illumination printed circuit board 43. The white LED light source 42 is made up of a plurality of white LED lamps spaced around a portion of an outer circumference of a light pipe 44. The light pipe 44 includes a dark light block 46 disposed around its outer circumference. The light block 46 prevents the white light source 42 from filtering into the inside of the light pipe 44 and interfering with the reflected light signal. When the measurement switch 26 is actuated, the white light source 24 illuminates, as indicated by arrows 48, a target area 50 on the color target 22. The target contact end 20 of the probe tip 18 surrounds the target area 50 of the color target. While the light pipe 46 is shown in the drawings as a primary way of receiving the reflected light signal, it can be appreciated that other optical devices can also be used for receiving the reflected light signal and projecting the signal onto a color light sensor.

The inside of the light pipe 44 captures reflected light, in the form of an analog light signal as indicated by dashed arrow 52, off the target area 50 and projects the captured light signal onto a 3 color (RGB) sensor 54 or tri-color photodiode. The sensor 54 is also mounted on the illumination printed circuit board 43. The 3-color sensor 54 collects the analog light signal, which is made up of percentages of red, green and blue. The percentages of color may be detected simultaneously or sequentially. While the use of the 3-color sensor 54 is discussed herein for measuring the primary colors of red, green and blue, it is appreciated that there are other color photodiode sensors for measuring magenta, yellow, cyan and black along with other colors. Therefore, the device 10 is not limited to measuring percentages of the primary colors of red, green and blue alone.

The analog light signal 52 is amplified and converted from an analog light signal to a digital light signal by an A/D converter. The A/D converter is incorporated into a printed circuit board 56. The printed circuit board 56 also includes a microprocessor and data storage memory. The digital light signal is transmitted from the microprocessor on the printed circuit board 56 to the liquid crystal display 30 or, as shown in FIG. 2, transmitted via the RS 232 electrical lead 36 to the computer 38 and visual display 40. It should be mentioned, that the microprocessor can include memory for storing multiple list of color samples and percentages of colors in the samples for providing a closest color match when displaying the percentages of color in the color target 22.

In FIG. 4, another side sectional view of the handheld portable color measuring device 10, as shown in FIG. 1, is illustrated. In this example, a 90-degree turning prism 58 is shown mounted on the end of the light pipe 44. The prism 90 is used to reflect the analog light signal 52 on to the 3-color sensor 54. The sensor 54 is mounted on the printed circuit board 56 and connected to the A/D converter. The turning prism 58 is shown to illustrate one of many ways the reflected analog light signal 52 can be transmitted to the 3 color sensor 54.

In FIG. 5, a circuit diagram of the optical and electrical components making up the color measuring device 10 is shown. The diagram includes an Opto module 60 made up of the white LED light source 42 and the 3 color sensor 54. The white light, transmitted by the LED lamps, is reflected off the target 22 and focused on the photodiodes of the sensor 54. The sensor converts the light energy to an electrical current proportional to the energy of the reflected light. The output from the Opto module 60 is illustrated as arrows identified as I red, I green, and I blue.

An ASP (Analog Signal Processor) module 62 converts the electrical current mode signals from the 3-color sensor 54 to voltage mode signals suitable for a DSP (Digital Signal Processor) module 64. An I-V (current to voltage) conversion 66 can be implemented with a trans-impedance amplifier or a standard op-amp. If necessary, a voltage amplification Av 68 can follow the I-V conversion 66. In addition, the ASP module 62 can provide a gain balance between the red, green and blue voltage channels. The output from the ASP module 62 is illustrated as arrows identified as V red, V green, and V blue.

The DSP (Digital Signal Processor) module 64 includes an AVR (AdVanced RISC) microprocessor 70. The microprocessor 70 includes a multi-channel A/D converter which converts the three voltage outputs from the ASP module 62 to a 10 bit digital representation. Programmed algorithms executed by the AVR microprocessor 70 accomplish the color data analysis. The DSP module 64 also controls the operational modes of a connected computer 38, monitors the color measurement switch 28 used to initiate the color measurement or calibrate the color measuring device 10, and controls the operation of the white LED light source 42, the 3 color sensor 54 and the LCD display 30. Also, the AVR microprocessor 70 can be used to perform system power management to preserve the life of the battery 35. The above mentioned ASP module 62 and the DSP module 64 are incorporated into the printed circuit board 56 shown in FIGS. 3 and 4.

A Power Supply block 72 contains the 6-volt battery 35 for providing the necessary voltage regulation for the analog and digital components and provides the necessary voltage for the LED lamps. Also, a separate low-dropout regulator is used for the Opto, ASP, DSP and the LCD components described above. The on/off switch 26 services two functions. It disconnects the load from the battery 35 to maximize battery life. Also, it provides the necessary variable state, which forces the AVR 70 into a calibration mode. When the switch 26 is cycled from an "off" to "on" position, the microprocessor's reset register will reflect this condition and will be programmed to enter into a calibration mode. At this time, the device 10 prompts the user to depress the measurement switch 28 to select a default calibration setting, or wait until prompted to calibrate a white standard. The white standard is contained with a white cap placed over the end of the probe tip 18. If the calibration is selected, the cap is held against the probe tip 18 and the measurement switch 28 is depressed. At this time, the calibration data in the microprocessor 70 is used to compare all future measurements of the target 22 until the switch 26 is turned "off". The device 10 is then calibrated each time the unit is turned "on".

Also shown in FIG. 5 is the LCD display 30 connected to the microprocessor 70 as shown solid arrows 74. Further, if the device 10 does not have the built-in display 30, the microprocessor 70 is connected to a personal computer as shown by dashed arrows 76.

Figure 6:
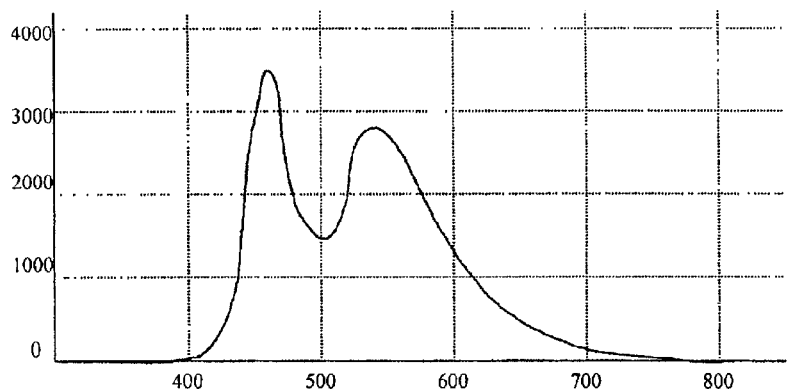
FIG. 6 is a spectral diagram of the white LED source over the range from 400 nm to 700 nm with intensity measured in counts and optical wavelength measured in nanometers.

In FIG. 6, an illustration of a white LED spectrum is shown. In this diagram the intensity levels of the white LED are over a range of 400 nm to 700 nm, with intensity measured in counts and optical wavelength measured in nanometers. This range is a typical color range detected by the human eye.

Figure 7:
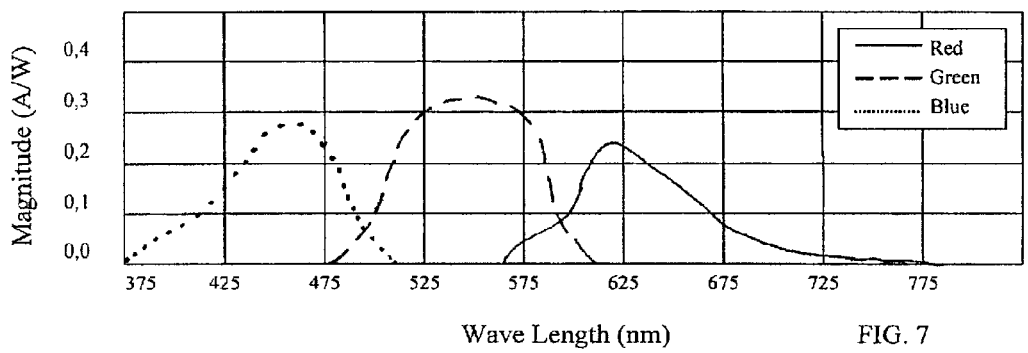
FIG. 7 is a typical spectral sensitivity of the 3-color sensor measuring blue, green and red color spectrums in optical wavelength and magnitude (A/W).

In FIG. 7, a typical spectral sensitivity of the 3-color sensor 54, used in the subject color measuring device 10, is shown measuring blue, green and red color spectrums in an optical wavelength (nm) and sensitiveness (A/W). In this example, the color blue is measured over a wavelength range of from 450 to 520 nm, the color green is measured over a wavelength range of 500 to 620 nm and the color red is measured over a wavelength range of 600 to 725 nm.

Figure 8:
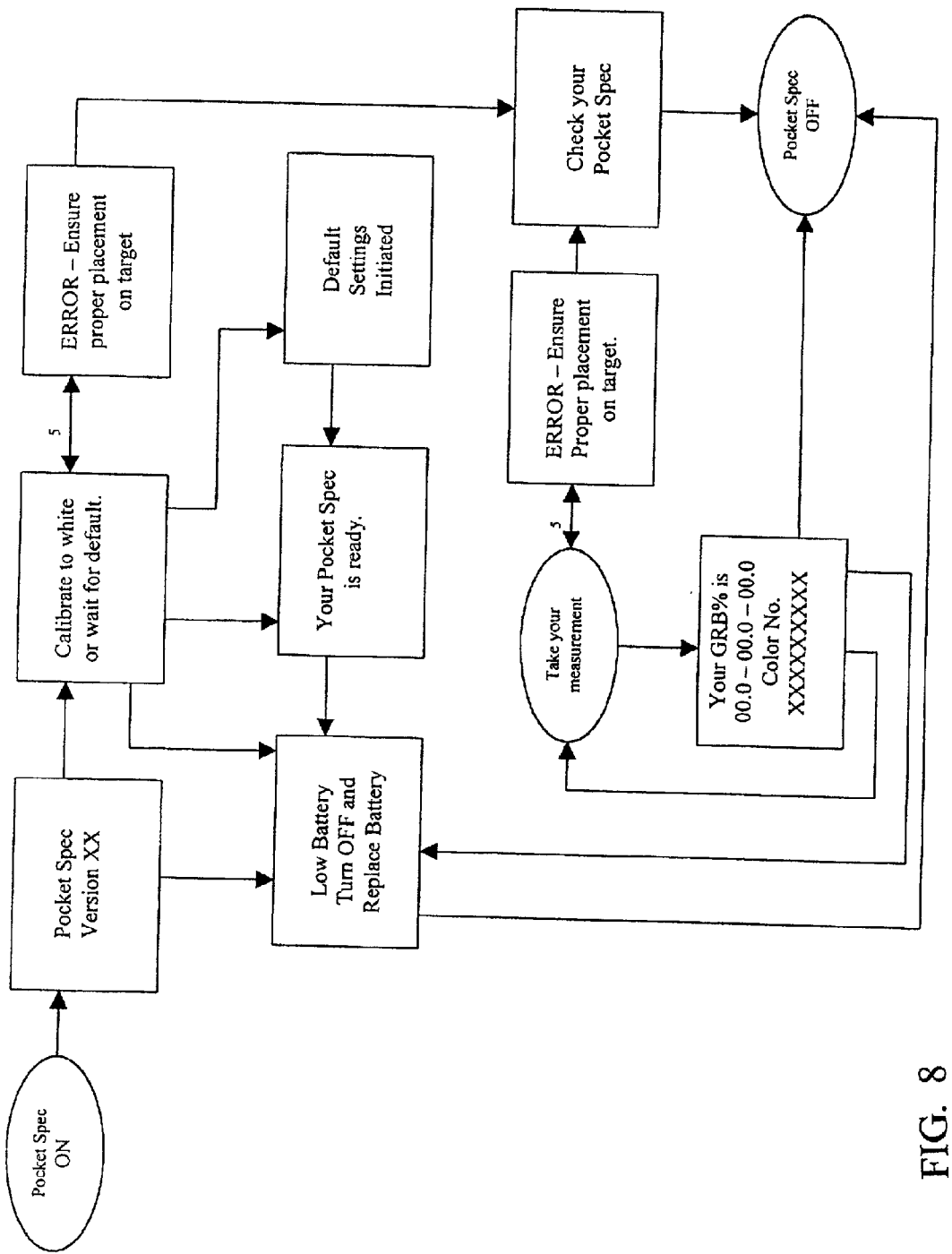
FIG. 8 is a diagram of the various states of operation of the color measuring device when the device is turned "on", the device is calibrated and a color measurement is taken and the device is turned "off".

In FIG. 8, a diagram of the various states of operation of the color measuring device 10 is shown. For example, when the on/off switch 26 is turned "on" a "PocketSpec version X.X" is displayed on the built-in display 30 or on the computer visual display 40. If the battery 35 is low, the display will state "Low Battery Turn Off and Replace Battery". If the battery 35 is not low, the display will state "Calibrate to White or Wait for Default".

If the decision to calibrate to a white standard is selected, the cap with white coating is placed around the probe tip 18 and the measurement switch 28 is activated. The device 10 is now calibrated until it is turned "off". If the user does not take action, the unit will revert to the default setting.

Once the calibration step has been completed, the device 10 is ready to measure colors. The last color measurement will remain displayed until the next color measurement is performed. For the device 10 that are connected to a computer, several measurements can be stored, but only the last measurement is displayed.

At any time during use, the device 10 will ensure that there is enough power in the battery 35, or display a "Low Battery" warning. Also, the device will warn the user if an error in measuring has occurred. For example, if the user takes a measurement while pointed toward ambient lighting, the color sensor 54 will saturate, and an error message is displayed.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A handheld, portable color measuring device for measuring three different colors in a color target to be analyzed, the color measuring device comprising:

a color measuring probe housing;

a hollow probe tip attached to one end of said probe housing, said probe tip adapted for placing next to the color target to be measured;

a white light source mounted inside the probe housing and connected to a power source;

a color measurement switch mounted on said probe housing and connected to said power source and connected to said light source, when said measurement switch is actuated said light source illuminating the color target surrounded by an end of said probe tip;

means for capturing a reflected light signal off the color target when the color target is illuminated, said means for capturing disposed inside said probe housing;

a multiple sensor mounted inside said probe housing, said 3 color sensor receiving the reflected light signal from said means for capturing;

a microprocessor mounted in said probe housing and connected to said power source and said 3 color sensor, said microprocessor for processing the reflected light signal; and display means connected to said microprocessor, said display means for displaying the reflected light signal in percentages of the 3 different colors.

2. The color measuring device as described in claim 1 wherein said display means is a built-in LCD display mounted in said probe housing.

3. The color measuring device as described in claim 1 wherein said light source is a white LED light source.

4. The color measuring device as described in claim 1 wherein said power source is a battery mounted inside said probe housing.

5. The color measuring device as described in claim 1 wherein said means for capturing is a light pipe centered inside said probe housing.

6. A handheld, portable color measuring device for measuring the primary colors of red, green and blue in a color target to be analyzed, the color measuring device comprising:

an elongated color measuring probe housing;

a hollow cone shaped probe tip attached to one end of the probe housing, said probe tip having a target contact end adapted for placing against the color target to be measured;

a white light source mounted inside the probe housing connected to a battery power source;

a color measurement switch connected to said battery power source and connected to said white light source, said white light source for illuminating the color target surrounded by the target contact end of said probe tip;

a light pipe centered inside said probe housing and inside a portion of said probe tip, said light pipe capturing a reflected light signal off the color target;

a 3 color (RGB) sensor connected to said battery power source and mounted inside said probe housing, said 3 color sensor receiving the reflected light received through said light pipe;

a microprocessor connected to said battery power source and mounted in said probe housing, said microprocessor connected to said 3 color sensor for processing the reflected light signal; and display means connected to said microprocessor, said display means for displaying the reflected light signal in percentages of red, green and blue.

7. The color measuring device as described in claim 6 wherein said display means is a built-in LCD display mounted in an opposite end of said probe housing, said microprocessor having memory with a coded list of colors with percentages of each primary color found in each color for providing a closest color match display when displaying the reflected light signal in percentages of red, green and blue on the LCD display.

8. The color measuring device as described in claim 6 wherein said light source is a white LED light source.

9. The color measuring device as described in claim 6 wherein said power source is a 6 volt battery mounted inside said probe housing.

10. A method for measuring at least three colors in a color target using a color measuring device, the color measuring device having a color measuring probe housing with a hollow probe tip adapted for placing next to the color target to be measured, a light source mounted inside the probe housing connected to a power source, a 3 color sensor connected to the power source and mounted inside the probe housing, a microprocessor with memory connected to the power source and a display screen connected to the power source, the steps comprising:

illuminating the color target next to the probe tip with the light source;

capturing a reflected light signal off the color target inside the probe housing;

measuring the reflected light signal on the 3 color sensor;

processing the 3 color sensor measurement using the microprocessor; and displaying percentages of the 3 colors from the color target on the display screen.

11. The method as described in claim 10 wherein the step of capturing the reflected light signal includes capturing the reflected light signal inside a light pipe received inside the probe housing and next to the 3 color sensor.

12. The method as described in claim 10 wherein the step of displaying percentages of the 3 colors includes displaying percentages of red green and blue found in the color target.

13. The method as described in claim 10 wherein the step of displaying percentages of the 3 colors includes displaying the percentages of the 3 colors on a built-in LCD display mounted on the probe housing.

14. The method as described in claim 13 further including the steps of storing in the memory of the microprocessor a coded list of various shades of colors with percentages of 3 different colors found therein and displaying on the LCD display a closest color match when compared to the percentages of the 3 colors from the color target.

15. The method as described in claim 10 wherein the light source is a white LED light source.

16. The method as described in claim 10 wherein the power source is a battery power source received in the probe housing.

* * * * *